United States Patent [19]

Shieh et al.

[11] Patent Number: 5,401,377

[45] Date of Patent: Mar. 28, 1995

[54] ION-SELECTIVE SENSOR WITH POLYMERIC MEMBRANE HAVING PHOSPHOLIPID DISPERSED THEREIN

[75] Inventors: Paul Shieh, Fremont; Dingli Guo, Newark; Shek-Hong Lau, Fremont, all of Calif.

[73] Assignee: Biomedix, Inc., Fremont, Calif.

[21] Appl. No.: 103,193

[22] Filed: Aug. 6, 1993

[51] Int. Cl.⁶ .................................................. G01N 27/26
[52] U.S. Cl. ...................................... 204/418; 204/403; 204/415; 435/817
[58] Field of Search ............... 204/403, 416, 418, 433, 204/435, 415; 435/817

[56] References Cited

U.S. PATENT DOCUMENTS

| | | | |
|---|---|---|---|
| 4,115,209 | 9/1978 | Freiser | 204/403 |
| 4,148,305 | 4/1979 | Reichenberger | 128/2 E |
| 4,399,002 | 4/1983 | Freiser | 204/403 |
| 4,490,216 | 12/1984 | McConnell | 204/403 |
| 4,637,861 | 1/1987 | Krull | 204/403 |
| 4,753,719 | 6/1988 | Yamaguchi | 204/418 |
| 4,776,944 | 10/1988 | Janata | 204/415 |
| 4,948,473 | 8/1990 | Phillippi | 204/153.2 |
| 4,959,130 | 9/1990 | Josowicz | 204/418 |
| 4,995,960 | 2/1991 | Wiles | 204/418 |
| 5,133,856 | 7/1992 | Yamaguchi | 204/416 |
| 5,139,626 | 8/1992 | Yamaguchi | 204/153.1 |
| 5,225,374 | 7/1993 | Fare et al. | 204/418 |
| 5,234,566 | 8/1993 | Osman et al. | 204/418 |

OTHER PUBLICATIONS

Cunningham, et al, "Coated Wire Ion Selective Electrodes", Analytica Chimica Acta, 180, 1986, pp. 272–274.

Cattrall, et al, "Coated Wire Ion Selective Electrodes," Ion-Selective Electrode Rev., vol. 6, 1984, pp. 126–128.

Primary Examiner—John Niebling
Assistant Examiner—Bruce F. Bell
Attorney, Agent, or Firm—Marvin S. Aronoff

[57] ABSTRACT

An ion-selective electrode having an ion-selective membrane in direct contact with an electrical conductor is provided in which the membrane coats an uninsulated zone surrounded by insulation on the surface of a conductor which is coated with a layer of electrical insulation. The membrane overlays the insulation surrounding the insulation free zone and comprises a polymer which is generally of sufficiently similar composition to that comprising the electrical insulation layer so that it adheres to the insulation forming a membrane with increased structural strength. Embodiments of the electrode containing phosphatidylcholine in the ion-selective membrane have increased sensitivity.

41 Claims, 8 Drawing Sheets

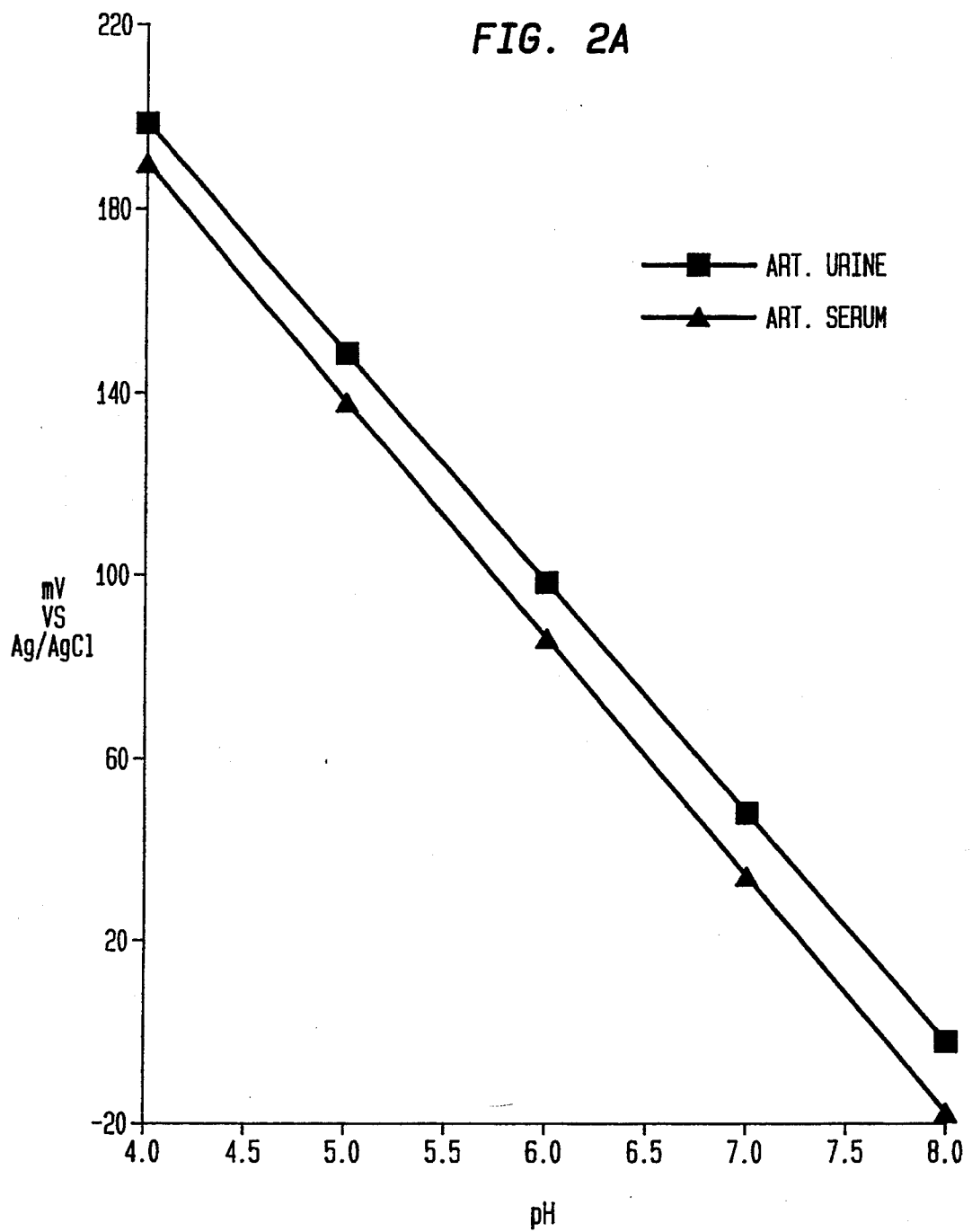

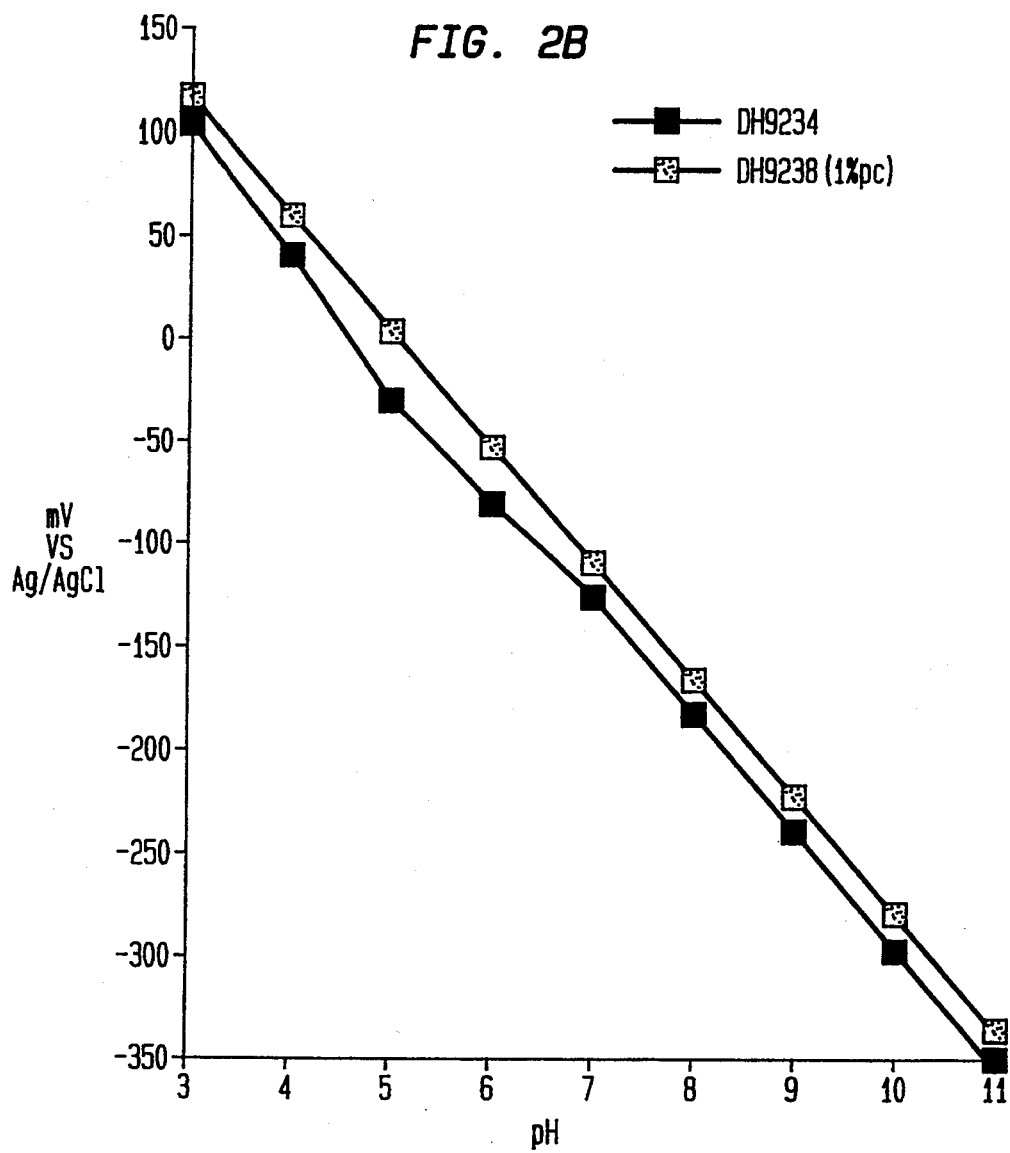

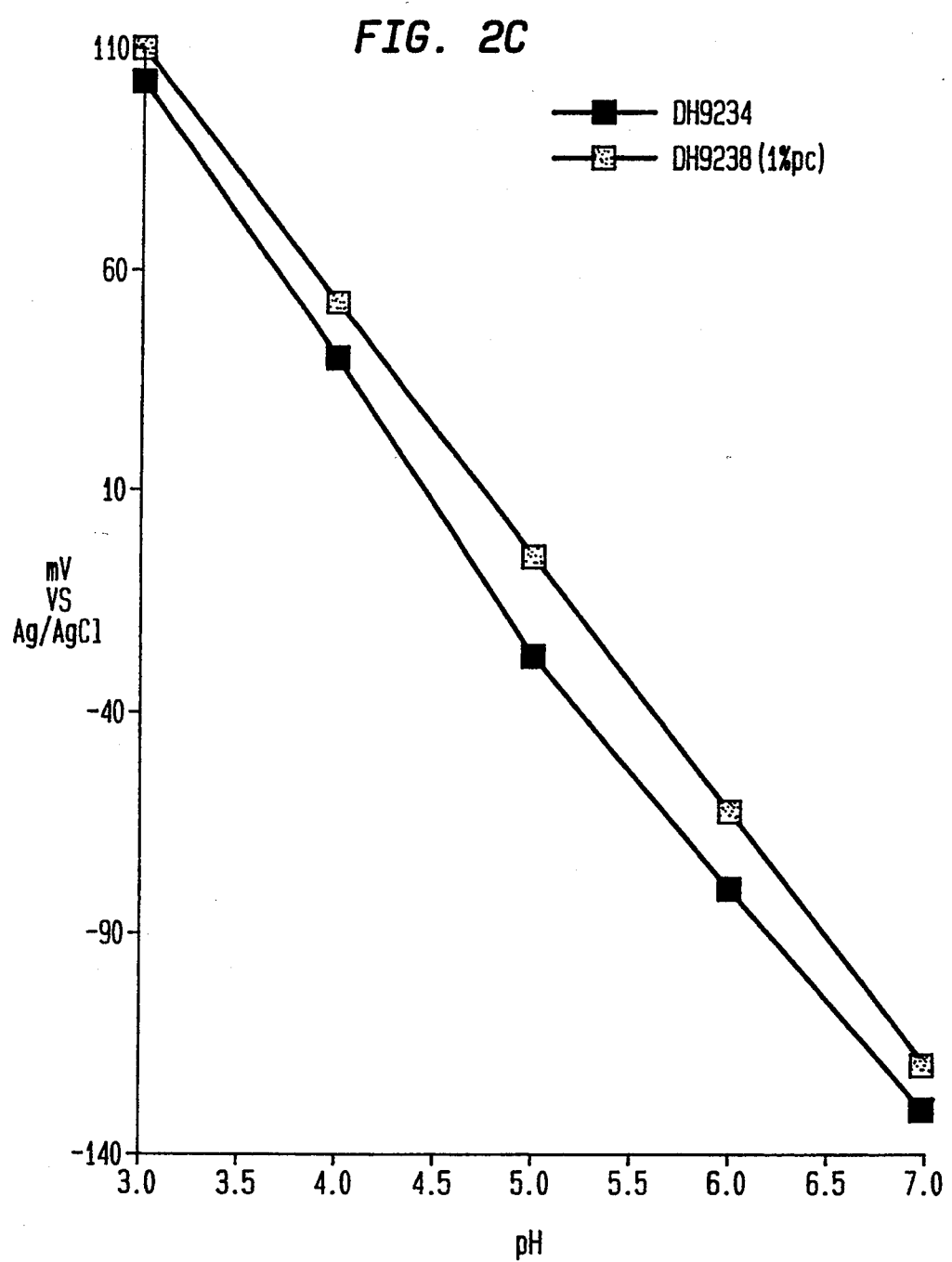

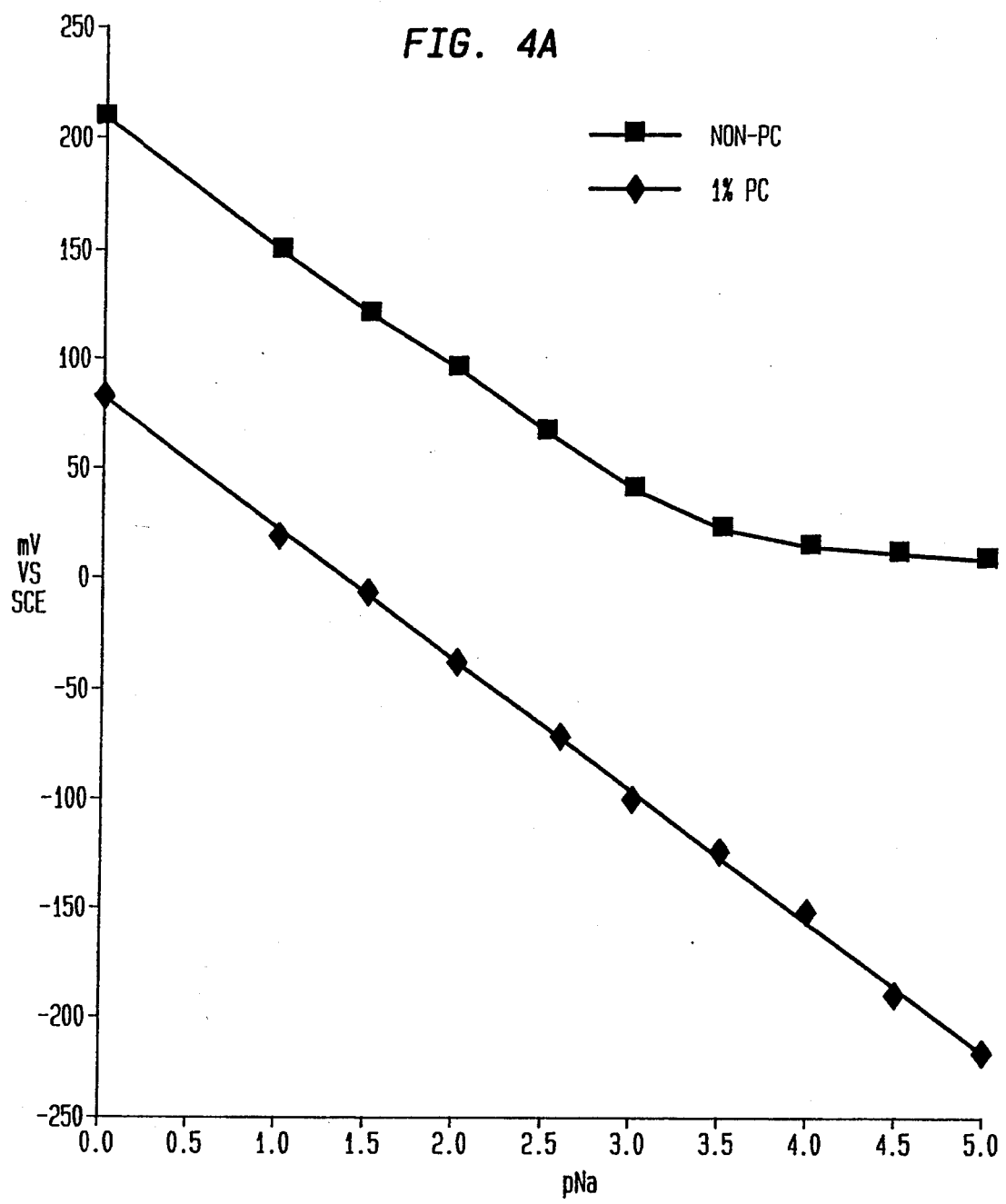

ION-SELECTIVE SENSOR WITH POLYMERIC MEMBRANE HAVING PHOSPHOLIPID DISPERSED THEREIN

BACKGROUND OF THE INVENTION

This invention relates to ion sensors, more specifically electrodes having an ion-selective membrane in direct contact with an electrical conductor.

Potentiometric assays of a specific ionic species in solutions containing other ions are well known in the art, and employ electrodes with a known response to the concentration of the ion to be assayed. Such electrodes are commonly termed ion-selective electrodes. In one class of such ion-selective electrodes, membranes having selective permeability to the ionic species to be assayed interface between the solution to be analyzed and the conductive member of the electrode. Among the types of material which have been used to form ion-selective membranes are ion-selective glass, ion-selective polymer and ion-selective water-immiscible liquid.

The ion-selective electrode is used in conjunction with a reference electrode to form an electrochemical cell by immersion in the solution to be analyzed. The potential which develops across this cell is proportional to the logarithm of the activity or the concentration in the solution of the ions to which the ion-selective electrode is sensitive. This potential is detected by an electromeric device, usually either a direct reading circuit or a null-balance potentiometric circuit.

Coated-wire electrodes are a type of ion selective electrode formed by coating a metallic wire or other electrical conductor with a polymeric ion selective membrane. They do not in general employ an internal reference electrode element, but membranes used on them can also be used on electrodes employing such an internal reference element. Coated wire electrodes and their preparation are described in detail by R. W. Cattrall and I. C. Hamilton in the article "Coated-Wire Ion-Selective Electrodes", Ion-Selective Electrode Rev., 1984, Vol. 6, pp. 125–172, incorporated herein by reference to the extent that it is pertinent. U.S. Pat. No. 4,948,473 also describes preparation of coated-wire electrodes and is incorporated herein by reference to the extent that it is pertinent.

The Nikolskii-Eisenman extension of the Nernst equation correlates electomotive force (EMF) or the measured potential with the activity or concentration of the specific ion in solution which can permeate the ion-selective membrane, in the presence of an interfering ion. This equation and an explanation of it are given by U. Oesch, D. Ammann and W. Simon in an article in the publication "Clinical Chemistry", 32/8, 1448–1459 (1986), which is incorporated herein by reference.

Ideally, for the specific ion, in a solution with other ions, for which an ion-selective electrode has exclusive selectivity, a plot of the negative logarithm of the concentration or activity of this species versus the measured potential in millivolts (mV) gives a straight line, which for monovalent ions has a theoretical slope of 59.2 at 25° or 58° at 20° C. Sensitivity to a specific ionic species is defined as the concentration range of the specific ionic species within which this relationship remains linear. The wider the linear response range of an ion-selective electrode, the more reliable and precise will be assays of the specific ionic species it detects.

Membrane forming phospholipids have been used as discrete layers in the construction of ion selective electrodes of various types. McConnell in U.S. Pat. 4,490,216 cites the use of bilayer forming phospholipids as the second layer of a membrane in an electroanalytical device. Krull et al in U.S. Pat. 4,637,861 discloses means to chemically anchor membrane forming phospholipid derivatives to oxidized electrolytic glassy carbon surfaces. Janata in U.S. Pat. No. 4,776,944 discloses a multi-layered active electrode in which selectivity is provided by either a natural lipid bilayer film obtained from plants or animals or a synthetic phospholipid film produced by the Langmuir-Blodgett process, either of which would include "gating" molecules which control the "opening" and "closing" of the film to the transport of ions.

In all cases of the above art, an effort is made to form an electrode in which the benefits of the phospholipid are derived from deliberately creating a discrete phospholipid monolayer or bilayer or maintaining such a structure originally derived from a plant or animal source.

Commercial application of coated wire electrodes and other electrodes employing an ion-specific polymeric membrane, for example, in the detection of ions in physiological fluids, environmental samples and in test kits intended for non-professional use, is restricted by a lack of reliability of the assay results. A critical cause of this lack of reliability is the failure of the linear detection range to extend far enough into the low concentrations which are of interest in the assay of for example, biological fluids, thereby reducing the accuracy and precision of the measurement.

An additional problem with electrodes of the coated wire type is mechanical instability of the ion selective membrane due to poor adhesion to the underlying conductive member.

Another factor impeding commercial application of coated wire electrodes is the lack of a simple, economical commercial process for their manufacture which reliably produces ion-specific electrodes with the same linear response range to a specific ion. Although coated wire electrodes are generally easier to prepare than conventional electrodes such as the barrel type, many steps are required and there may be significant variation in sensitivity and precision of electrodes both within and between batches detracting from the efficiency of commercial production.

Limited shelf life and operational lifetime also restrict the commercial utility of such electrodes.

A further problem preventing wider use of coated wire ion-selective electrodes is that they are too difficult for use by lay personnel. For example, ion-specific electrodes having linear response over a relatively narrow range are more complicated to calibrate than whose response is linear over a wide range.

Yet another problem with existing coated wire electrodes prepared by present processes is difficulty in achieving an optimally miniaturized configuration of the active electrode site.

For the foregoing reasons there is a need for ion-selective electrodes with wide linear response range which can be easily miniaturized and used and a process to produce them inexpensively with a high degree of reliability and consistency.

BRIEF DESCRIPTION OF THE INVENTION

The present invention is directed to improving the reliability, sensitivity, and mechanical stability of coated wire ion-selective electrodes and other electrodes having an ion-selective membrane in direct contact with an electrical conductor.

A further object of the invention herein disclosed is to provide simple and economical means of commercially producing coated wire ion sensors and other electrodes having an ion-selective membrane in direct contact with an electrical conductor, with consistent response.

Yet another object of the invention is to provide miniaturized and disposable selective ion sensors.

Still another objective is extension of the shelf storage life and operational lifetime of such selective ion sensors.

The above and other objects are achieved in accordance with the present invention by providing an ion selective electrode with linear Nernstian response over a wide range which is durable, can be miniaturized and is easily manufactured and used.

Such an ion-selective electrode for measuring the concentration of a specific ion in a solution comprises: an electrically conductive member sheathed or coated with a layer of insulation in direct contact with said electrically conductive member, except at a zone on its surface which is surrounded by the insulation, with the zone free of insulation, an ion selective membrane, said membrane comprising; a polymeric matrix, the polymeric matrix having dispersed or dissolved therein; a plasticizer, an ionophore, and a phospholipid chosen from the group consisting of:

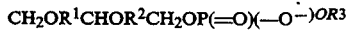

wherein $R^1$, and $R^2$ are acyl groups derived from saturated or unsaturated fatty acids having from 6 to 24 carbon atoms, and $R^3$ is $-CH_2CH_2N(R^4)_2$ and the protonated form thereof, $-CH_2CH_2N^+(R^4)_3$ or $-CH_2CHN(R^4)_2CO_2H$ and charged forms thereof, wherein $R^4$ is chosen from the group consisting of H, alkyl groups having from 1-14 carbon atoms or benzyl in any combination, and $R^3$ is further inositolyl, $-CH_2$-$CHOHCH_2OR_5$ wherein $R_5$ is H or $CH_2OR^1CHOR^2C$-$H_2OP(=O)(-O)-$ and protonated forms thereof; sphingomyelin and mixtures thereof, said ion selective membrane forming a coating which envelops the surface of the uninsulated zone of the electrically conductive member and overlays and further coats and adheres to the surrounding electrical insulator generally adjacent to the uninsulated zone.

In one embodiment of the invention, the electrically conductive member is a core member and, the core member is a metallic wire covered with a layer of electrical insulation and in direct contact with the insulation. The ion selective membrane coats the zone of the metallic wire exposed at one end and the coating overlays the surrounding electrical insulation generally adjacent to the coated metallic wire. The membrane comprises a polymer matrix in conjunction with a plasticizer, and an ionophore to permit permeation of a specific ion of interest in an aqueous solution. In other embodiments the membrane additionally comprises a phospholipid in effective amount to increase sensitivity to the specific ion and, in yet other embodiments the membrane comprises at least one additional signal enhancing component.

In yet another embodiment of the invention, the electrically conductive member is a metallic strip covered with insulation except at a selected zone which forms an insulation free island surrounded by insulation on the surface of the metallic strip. The zone is coated by the ion-selective membrane which overlays and adheres to the surrounding insulation generally adjacent to this zone.

In still another embodiment, the electrically conductive member is a conductive layer or strip on an electrical circuit board base, with the surface of the conductive layer covered with a layer of electrical insulation, except for a selected insulation free zone, which is surrounded by insulation. The insulation free zone is coated with an ion-selective membrane which overlays and adheres to the surrounding electrical insulation generally adjacent to that zone. In practice, the electrically conductive layer is generally metallic.

A convenient and economical process for manufacture of an ion selective electrode for use in determining the concentration of specific ions in solution is also provided. The process generally comprises the steps of forming an electrically insulated electrically conductive member having an insulation free zone surrounded by the insulation; making a liquid solution of an ion-selective membrane formulation by mixing a polymer which is able to adhere to the electrical insulator, a plasticizer and, an ionophore in a solvent; coating the insulation free zone and the insulation generally adjacent to said zone with the liquid solution so that the liquid solution forms a coating which envelops said zone and overlays the generally adjacent surrounding insulation; and evaporating the solvent to form an ion selective membrane which coats and generally adheres to the insulation free zone of the conductive member and overlays and adheres to the surrounding electrical insulation generally adjacent to said zone, thereby forming a structurally strong ion-selective membrane.

In one embodiment of the process the insulated conductive member is an insulated metallic wire and exposed metal at a tip of the wire is an insulation free zone. Generally the wire and surrounding insulation are approximately flush, however, the wire may protrude slightly from the surrounding insulation or may be recessed slightly relative to the surrounding insulation. In this embodiment, the process produces a coated wire electrode by forming an ion-selective membrane which completely coats and generally adheres to the metal at the tip and overlays and strongly adheres to the insulation generally adjacent to said tip.

In a further version the metal at the tip of the wire may be covered with insulation and at a selected zone along the length of the insulated wire, the insulation is removed to form an insulation free zone on which the membrane is formed which completely coats the zone and overlays and adheres to the generally adjacent insulation.

In another embodiment of the process the insulated conductive member is a metallic strip on a circuit board which is coated with a layer of insulation except for a selected zone on its surface which remains free of insulation although surrounded by the insulation. The metallic strip on the circuit board may itself be a laminate comprising a layer of conductive base metal such as copper which is covered with a thin layer of nobel metal such as gold. The insulation free zone and the surrounding insulation generally adjacent to the zone is coated with the solution of membrane formulation which on drying forms a structurally strong ion-selective membrane at this zone. This embodiment may comprise a component of miniaturized electrolytic cell by forming a reference electrode such as a silver-silver chloride electrode on a separate metallic strip adjacent to the metallic strip having the ion-selective electrode. When the ion-selective electrode and the adjacent reference electrode on the circuit board are electrically connected through potentiometric sensing means and are simultaneously exposed to a solution containing ions to which the ion-selective membrane is sensitive a potential proportional to the concentration of the ion is generated as earlier described. Such a miniaturized cell may comprise part of a kit to be used in detecting the concentration of an ion of interest in materials such as biological fluids and for titrations.

A further version of the process generally comprises the steps of cutting through the insulation and metal of an insulated metallic conductor to expose a fresh metallic surface, preparing a liquid solution of an ion selective membrane formulation containing a polymer, solvent, plasticizers, specific ion sensing ionophores and a phospholipid, immersing the exposed metallic tip in the solution to completely coat it, and evaporating the solvent from the coating to form an ion selective electrode.

An important advantage of this version of the present invention is that it provides ion selective electrodes with linear Nernstian response over a considerably widened concentration range thus making assay of specific ions such as those found in physiological fluids and environmental samples more reliable. A further advantage of the widened linear Nernstian response range of the electrodes of the present invention is that a single point can be used for calibrating them against a solution containing a known concentration of the ion to be detected, thus increasing their ease of use and shortening the time needed to prepare for a measurement.

Yet another advantage of the ion sensing electrodes of the present invention is that they are made by an economical process which produces electrodes with consistent characteristics. The process also allows for creation of an ion-selective electrode on an extremely small area of an electrical conductor thus facilitating miniaturization. An additional advantage is that mechanical stability is achieved by creating an ion-selective membrane which is generally adherent to the underlying conductive member and adheres to the electrically insulating material which coats the conductive member. This improved mechanical stability makes the ion sensors of the present invention less fragile and easier to manufacture and use. A further advantage of improved mechanical stability is extended shelf life as well as increased operational lifetime.

BRIEF DESCRIPTION OF THE DRAWINGS

These and other features, aspects, and advantages of the present invention will become better understood with regard to the following description, appended claims, and accompanying drawings where:

FIG. 2A shows a graph of the response of a pH sensing electrode version of the present invention in artificial serum and in artificial urine.

FIG. 2B shows a graph comparing the response of pH sensing electrode versions of the present invention.

FIG. 2C shows a partially enlarged view of FIG. 2B.

FIG. 4A shows a graph comparing the response of sodium ion sensing electrode versions of the present invention.

DESCRIPTION OF THE PREFERRED EMBODIMENTS

Figure 1:
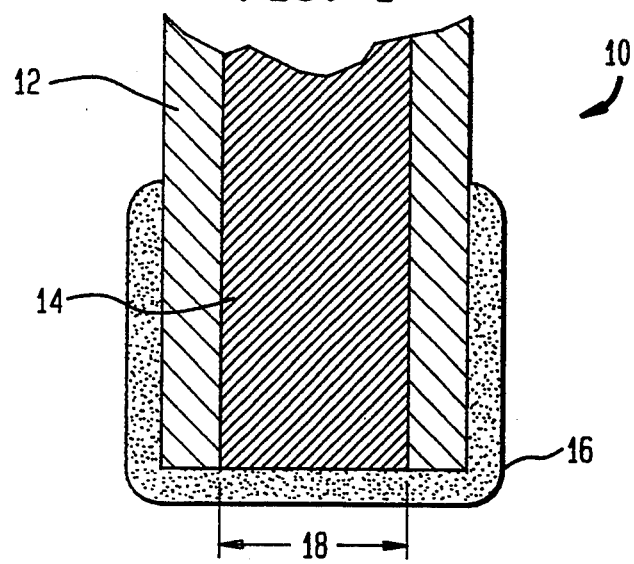
FIG. 1 shows a cross-sectional view of a version of an ion sensing electrode of the present invention.

The following abbreviations used in the description of different embodiments of the invention are hereby defined:

PVC-Polyvinylchloride
THF-Tetrahydrofuran
NPOE-2-Nitrophenyl octyl ether
DOS-Bis(2-ethylhexyl) sebacate
DBP-Dibutyl phthalate
CB-Chlorobenzene
TPB-Potassium tetrakis(4-chlorophenyl) borate
TDDA-Tridodecylamine
CMMDM-bis([12-crown-4]-2-methyl)2-methyl-2-dodecylmalonate
PC-Phosphatidylcholine FIG. 1 is a cross-sectional view of an ion sensing electrode 10 which is an embodiment of the present invention. The electrode 10 is generally a coated wire electrode and includes an electrically conductive member which in this embodiment is a core member 14, an electrical insulation layer 12, and an ion-selective membrane 16, formulated in the manner described below, which completely coats an uninsulated or exposed zone which is surrounded by insulation at tip 18 of the conductive core member 14 and overlays and adheres to a portion of the insulation layer 12. In practice, the core member 14 is comprised of wire made of copper, which is preferred, but silver, conductive carbon, gold, aluminum, platinum, nickel, stainless steel, iron and other conductive materials and mixtures or coatings thereof can be used. Copper wire of 12–26 gauge is preferred with 18–24 gauge more preferred to obtain a miniature electrode on a convenient base. The body of the conductive core member 14, except the exposed tip 18, is sheathed by the electrical insulation layer 12. In practice, the electrical insulation layer 12 is comprised of PVC, but copolymers of PVC, polymers generally belonging to the PVC family and other polymers compatible with PVC and mixtures thereof and, polyethylene, polypropylene, nylon, polytetrafluoroethylene, copolymers of tetrafluoroethylene with ethylene and propylene, silicone rubber, and other electrical insulating materials may be used. However insulating materials comprised of PVC, copolymers of PVC and polymers compatible with PVC are preferred. The uninsulated zone of the conductive core 14, the exposed tip 18, is completely coated with the ion-selective membrane 16, prepared in the manner described below, which adheres to it in some degree and, is generally more strongly adherent to the insulation layer 12 which it overlays. The membrane 16 may overlay insulation layer 12 to any extent necessary to provide sufficient mechanical strength and overall adhesion to insulation layer 12, but an overlay generally adjacent to tip 18 is preferred as this uses less material and facilitates handling.

Figure 1A:
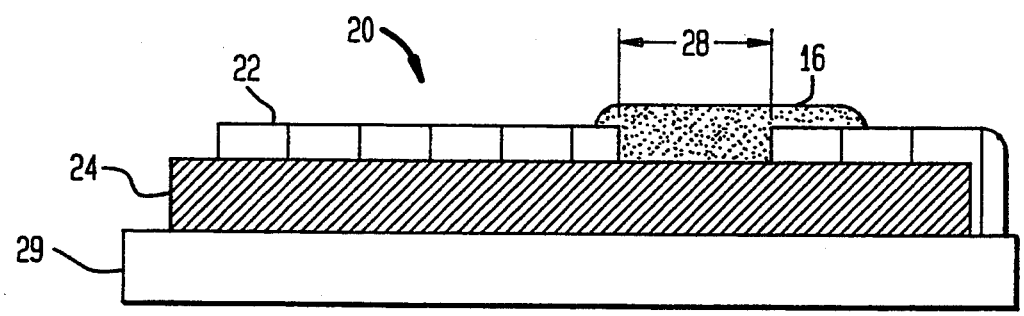
FIG. 1A shows a cross-sectional view of another version of an ion sensing electrode of the present invention.

FIG. 1A is a cross-sectional view of another embodiment an ion sensing electrode of the present invention. The electrode 20 is generally a circuit board electrode and includes a thin strip or layer of an electrically conductive member 24 on a circuit board base 29, an electrical insulation layer 22, which coats the electrically conductive member 24, except at an uninsulated zone surrounded by insulation 28, on the surface of the electrically conductive member 24, and an ion-selective membrane 16, which completely coats the uninsulated zone which is surrounded by insulation 28 of the conductive core member 24 and overlays and adheres to a portion of the insulation layer 22 generally surrounding the zone 28. The ion-selected membrane is formulated in the manner described below.

The materials for the electrically conductive member 24 are generally the same as for electrode 10. The electrically conductive member 24 may, however, be a laminate of at least two layers of metal, for example a layer of base metal coated with a thin layer of noble metal. A laminate comprising a layer of copper with a thin outer layer of gold is preferred for electrically conductive member 24. Any means known in the art may be used to hold electrically conductive member 24 in contact with the circuit board base 29. The materials for the insulation layer 22 of this embodiment are generally the same as for the embodiment of FIG. 1, with insulating materials comprising PVC preferred. The circuit board base 29 may be of any material known in the art, with materials to which the membrane 16 is adherent preferred.

In general the base material for the membrane 16 is a polymer matrix. The polymer is preferably PVC or other non-polar, relatively water insoluble polymers such as polyvinyl butyryl, polyvinylidene chloride, polyvinyl fluoride, polyvinylidene fluoride, polyvinyl bromide, polyvinylidene bromide, copolymers of polyvinyl alcohol with an appropriate comonomer such that the copolymer is insoluble, polymethyl methacrylate and copolymers thereof, epoxy resins, polyurethanes, poly(fluorophosphazenes), block copolymers of poly(dimethylsiloxane) and polystyrene, polyamides, polyimides and silicone rubber. A polymer which is generally of sufficiently similar composition to that comprising the electrical insulation layer 12, so that it is capable of adhering to the insulation, is more preferred.

To form the membrane 16 a liquid mixture is made by dissolving or dispersing the polymer base material, an ionophore sensitive to the ion of interest and a plasticizer in a suitable solvent. In other embodiments of the invention, an effective quantity of a phospholipid to provide a wider range of linear Nernstian response is added. In addition, a signal enhancing material or a combination of such materials such as TPB, sodium tetraphenylborate, iodine, α-carotene and other hydrocarbon materials having conjugated double bonds may be added to the liquid mixture depending on the ion to be detected. For example, TPB is added to the mixture for pH sensing and K+ ion sensing electrodes. This liquid mixture is then used in the electrode forming process in the manner described in the following.

A version of a process according to the present invention for making an embodiment corresponding to electrode 10 generally comprises the steps of, preparing a fresh conductive surface by cutting through the insulation 12 and the conductive core 14 of an insulated metallic wire thereby exposing a fresh metallic surface at the tip 18; preparing a liquid solution of an ion selective membrane formulation containing a polymer, solvent, plasticizer, and specific ion sensing ionophores; completely coating the exposed metallic tip 18 and the insulation layer 12 adjacent to it, by immersing the tip 18 and the adjacent insulation layer in the liquid solution of an ion selective membrane formulation; and, evaporating the solvent from the coating to form an ion selective membrane 16 at the tip 18, of electrode 10. In a further embodiment, a phospholipid or mixture of phospholipids is added in effective amount to the membrane formulation to extend the range of linear Nernstian response, and in yet other embodiments where appropriate, signal enhancing additives are added to the membrane formulation.

The electrode 10 can be optionally pre-activated by exposing membrane 16 to a solution of the ion to be detected. The resultant electrode can be used directly or is optionally stored in an environment saturated with the vapor of the plasticizers used in the membrane formulation.

In the cutting step any device such as conventional hand held wire cutters, a chromatography cutter or any machine which can cut wire or which is capable of cutting through the insulating layer 12 and the conductive core 14 thereby exposing a fresh surface of the conductive core 14 and creating the exposed conductor tip 18 may be used. The cut surface may in general be of any geometry but a generally flat planar surface for exposed conductor tip 18 is preferred. In the case of a coated wire electrode a configuration in which the exposed conductor tip 18 created by cutting through insulating layer 12 and conductive core 14 has a generally flat planar surface which is generally perpendicular to the longitudinal axis of conductive core member 14 is most preferred, as this provides a base on which the membrane 16 can be formed with relatively uniform thickness.

In the membrane formulation solution step the polymer used may be any polymer which is capable of forming a semi-permeable membrane from a solution or dispersion in a solvent such as PVC, polyvinylidene chloride, acrylic polymers and copolymers, cellulose acetate, nylons, polyphenylene oxides, polyacetals, polyesters, polycarbonates, polyethylene, polypropylene, polyimide, polyphenylene oxide, polystyrene, polysulfone, polyurethanes and silicone resins. Polymers such as PVC, polyurethanes, polyvinylacetate and its copolymers, ethylene vinylacetate copolymers, polyethylmethacrylate, terpolymers of vinyl chloride, vinylacetate and vinyl alcohol are more preferred as they can be readily dissolved or dispersed in common solvents such as THF, acetone, dimethylformamide, methylethyl ketone, cyclohexanone, chloroform, carbon tetrachloride, methylene chloride and benzene. PVC and copolymers in the PVC family having medium to relatively high molecular weight are most preferred as they give solutions of workable viscosity from which the membrane 18 can be obtained with good mechanical strength. To achieve a superior level of mechanical strength from the membrane 16, the polymer used should also preferably be sufficiently compatible with the material from which the insulation layer 12 is formed so that the membrane 16 is adherent to the insulation layer 12.

Any solvent such as THF, acetone, dimethylformamide, methylethyl ketone, cyclohexanone, chloroform, carbon tetrachloride, methylene chloride and benzene or any mixture of these or any other solvent which is capable of dissolving or dispersing the polymer and other ingredients may be used in the membrane formulation solution step, but solvents such as THF, cyclohexanone, chloroform and dimethylformamide and THF are preferred as they are easily removed, for example, by evaporation from the membrane 16. To achieve a superior level of mechanical strength from the membrane 16, the solvent used will also preferably soften the insulation layer 12 thereby promoting adhesion to it of the membrane 16. The quantity of any solvent used in the membrane formulation solution step depends on the type of polymer used as well as the other components used in the membrane formulation. In practice the weight of solvent ranges from about 30% to about 95% of the total solution weight. A solution or dispersion with a viscosity which is such that a thin uniform film can be formed at the exposed conductor tip 18 is preferred. When the film or membrane forming polymer is PVC, and the solvent is THF, the weight of solvent in the membrane formulation solution step is preferably from about 40% to about 90% and more preferably from about 50 to about 85%. In practice THF or other volatile solvent may be evaporated from a membrane forming solution whose viscosity is too low to form a satisfactory film at exposed conductor tip 18, for example by exposure to ambient air, to obtain a solution viscosity which gives a thin uniform film.

The materials used in conjunction with the polymer in the membrane formulation solution step will depend on the specific embodiment of the invention. When the film or membrane forming polymer is PVC or a related polymer, plasticizers for PVC and related polymers such as 2-nitrophenyl alkyl ether, phthalic acid derivatives such as DBP, dioctylphthalate and dipentylphthalate, sebacic acid derivatives such as di-n-alkyl sebacate and oxalic acid derivatives and mixtures thereof may be used. Preferred plasticizers are NPOE, DOS, DBP. Although selection of a plasticizer will depend upon the polymeric material used in the membrane, the plasticizer generally should be a material that lowers the glass transition temperature, Tg, of the polymeric membrane material below normal operating temperature (e.g. about 15°–45° C.) when added in a plasticizing-effective amount. The percentage of the weight of polymer based on the total weight of plasticizer and polymer ranges from at least 90% to about 10% and, preferably, is within the range of about 20% –40%.

The specific ion to be sensed by an embodiment of the invention will determine the ionophore added in the membrane formulation solution step. Typically, for an embodiment to sense hydrogen ions or pH, a hydrogen ion sensitive ionophore is added in the membrane formulation solution step. Such ionophores include TDDA, 4-nonadecylpyridine, N,N-dioctadecylmethylamine, octadecylisonicotinate and mixtures thereof but TDDA is preferred. When TDDA is the ionophore, the weight percentage of TDDA based on the total of the weights of all components comprising the membrane formulation but excluding the weight of the solvent used to make the membrane formulation solution ranges from about 0.5% to about 10%; preferably from about 1% to about 7%; more preferably from about 2% to about 5%.

For an embodiment to sense potassium ions, a potassium ion sensitive ionophore is added in the membrane formulation solution step. Such ionophores include valinomycin, bis[(benzo-15-crown-5)-4'-ylmethyl]pimelate, dimethyl dibenzo-30-crown-10, 4-nitrobenzo-18-crown-6 and mixtures thereof with valinomycin preferred. When valinomycin is the ionophore, the weight percentage of valinomycin based on the total of the weights of all components comprising the membrane formulation but excluding the weight of the solvent used to make the membrane formulation solution ranges from about 3% to about 10%; preferably from about 4% to about 8%; more preferably from about 5% to about 7%.

For an embodiment to sense sodium ions, a sodium ion sensitive ionophore is added in the membrane formulation solution step. Such ionophores include CMMDM, N,N', N"-triheptyl-N,N',N"-trimethyl-4,4'4"-propylidynetris (3-oxabutyramide), N,N'-dibenzyl-N,N'-diphenyl-1,2-phenylene-dioxydiacetamide, N,N,N'N'-tetracyclohexyl-1,-2-phenylene-dioxydiacetamide, 4-octadecanoloxymethyl-N,N,N',N'-tetracyclohexyl-1,2-phenylenediacetamide and mixtures thereof, but CMMDM is preferred. When CMMDM is the ionophore, the weight percentage of CMMDM based on the total of the weights of all components comprising the membrane formulation but excluding the weight of the solvent used to make the membrane formulation solution ranges from about 3% to about 20%; preferably from about 6% to about 15%; more preferably from about 8% to about 12% and most preferably about 10%.

To produce an embodiment with increased sensitivity, phospholipids are added in the membrane formulation solution step in quantities which are effective in extending the range of linear Nernstian response. The phospholipids may be PC, phosphatidylethanolamine, phosphatidylserine, phosphatidylinositol, phosphatidylglycerol, cardiolipin, sphingomyelin and mixtures thereof, or any other phospholipid or mixture of phospholipids of natural or synthetic origin which when added to the membrane formulation of an ion-selective membrane, in effective amount extends the sensitivity of the resultant ion-selective membrane. PC is preferred as it is readily available, and can easily be dissolved or dispersed in solvents such as THF used in the membrane formulation solution step. PC of synthetic or natural origin, as a pure material or a mixture may be added in effective amount to the membrane formulation solution. The added PC may be obtained by extraction or fermentation from soy beans and from other biological sources. Examples of PC of animal or plant origin which may be used include egg yolk lecithin preparations; hydrogenated egg yolk lecithin preparations; extracts of animal organs, such as brain, liver and, heart; mixtures obtained from soybean sold by Sigma such as Type II-S which has PC content 10–20% based on choline determination and contains many other lipids, Type IV-S which has PC content approximately 40% and, Type III-S which has PC content approximately 99% and is supplied as a chloroform solution containing 100 mg/ml. PC in mixtures obtained from soy bean is more preferred as it more economical to use. Sigma type II-S is most preferred as it is most economical. The weight percentage of PC based on the total of the weights of all components comprising the membrane formulation but excluding the weight of the solvent used to make the membrane formulation solution ranges from about 0.01% to about 20%; preferably from about 0.05% to about 10%; more preferably from about 0.1% to about 5% and most preferably from about 0.1% to about 3%. Although the phospholipids used in embodiments of the present invention are generally homogeneously dispersed in the membrane formulation solution, they may not necessarily remain homogeneously dispersed within the polymer matrix of membrane 16, but may, to some degree, spontaneously form a monolayer on its surface or a bilayer when exposed to water.

In some embodiments, signal enhancing materials are added in the membrane formulation solution step. In the case of the hydrogen ion electrode and potassium ion electrode embodiments, the signal enhancing material may be TPB, sodium tetraphenylborate and mixtures thereof. When TPB is used, the weight percentage of TBP based on the total of the weights of all components comprising the membrane formulation but excluding the weight of the solvent used to make the membrane formulation solution ranges from about 0.002% to about 20%; preferably from about 0.02% to about 2% and more preferably from about 0.01% to about 1%.

In the case of the potassium ion electrode embodiment an additional signal enhancing substance such as CB, nitrobenzene, 1,2-dimethyl-3-nitrobenzene, benzylether and mixtures thereof may also be added in the membrane formulation solution step. When CB is the additional signal enhancing substance, the weight percentage of CB based on the total of the weights of all components comprising the membrane formulation but excluding the weight of the solvent used to make the membrane formulation solution ranges from about 0.01% to about 10%; preferably from about 0.05% to about 5%. In yet another version of the potassium ion electrode embodiment nitrobenzene as well as CB is added in the membrane formulation solution step. The weight percentage of CB when used together with nitrobenzene is preferably the same as when it is used alone, and the weight percentage of nitrobenzene preferably is approximately equal to the amount of CB used.

Shaking and gentle heating may be used to form a uniform solution or dispersion of the ion-selective membrane forming components. The membrane forming solution may be freed of bubbles by gentle heating or shaking or by mechanical stirring or low level sonication or by other means familiar to those skilled in the art, before coating the exposed conductor tip 18, to avoid defects and non-uniformity of membrane thickness in the membrane 16.

In the coating step a cohesive coating of generally uniform thickness is preferred so that the membrane 16 will be generally symmetrical and uniform. In the case of a coated wire electrode this may be achieved by keeping the long axis of the wire in a generally vertical position while dip coating exposed metallic tip 18 and while subsequently drying the coating.

During dip coating the exposed metallic tip 18 is quickly immersed in the solution to a depth and for a duration sufficient to completely coat it. For example, with a 24 gauge copper wire insulated with PVC, immersion to a depth of about 0.1 mm to about 10 mm with about 1 mm to about 5mm preferred, for a few seconds in a solution containing approximately 25% to about 30% by weight of membrane formulation in THF, when the membrane formulation by itself has approximately 25% PVC will completely coat it.

After dip coating, solvent is removed from the coating by evaporation in air or by other means. When the solvent is THF and the membrane formulation contains approximately 25% PVC and the formulation comprises about 25% to about 30% by weight of the solution, the solvent is removed by evaporation in air for about 5 to about 120 minutes with about 10 to about 45 minutes preferred.

The number of dip coating, drying cycles may vary from 1 to 25 depending on the viscosity and concentration of the membrane formulation solution, the polymer matrix, solvent and other ingredients used. Dip coating and drying is repeated as many times as necessary to obtain the membrane 16 with sufficient thickness to provide adequate mechanical strength and good electrical response. With membrane formulations in which the polymeric component is PVC, the membrane 16 should have a thickness of preferably about 0.01 mm to about 1 mm, more preferably about 0.05 to about 0.5 mm and most preferably about 0.1 to about 0.3 mm. Dip coating is preferred for embodiments having the configuration of electrode 10 but other methods may be effective for applying the membrane formulation solution to form the membrane 16 and may be preferred for other electrode configurations and include spin coating, spray coating, painting and printing, as well as, variants and combinations of these and other processes familiar to those skilled in the art.

After coating, the electrode 10 may be used directly, but preferably is allowed to dry to remove residual solvent from the membrane 16 to obtain reliably good response performance. When membrane 16 is based on PVC and THF was used as the solvent for the membrane formulation, the electrode 10 can be air dried from about 6 hours to about 16 hours under ambient conditions. Other processes suitable for drying such as storage in an oven heated to below the boiling point of the solvent used in dissolving the membrane formulation or conveying through a series of ovens of suitable temperature or exposure to infrared heaters or other sources of radiant heat, and vacuum drying may be applied in the drying step. The degree of drying achieved, however, should preferably be approximately that achieved by air drying.

The electrode 10 may be optionally stored in containers saturated with the vapor of the plasticizer used in the formulation for membrane 16 in order to extend its shelf life.

A version of the process according to the present invention for making an embodiment corresponding to the circuit board electrode 20 comprises selecting a zone on a conductive strip 24 which is mounted on a circuit board base 29, the conductive strip covered with insulation 22; removing the insulation layer 22 from the selected zone to form uninsulated zone 28 surrounded by insulation, which has a fresh conductive surface; preparing a liquid solution of an ion selective membrane formulation containing a polymer, solvent, plasticizer, and specific ion sensing ionophores; coating the uninsulated zone 28 with the membrane formulation solution so that the coating completely envelops the surface and periphery of the electrically conductive strip 24 within zone 28 and, overlays the surrounding insulation layer 22 adjacent to the zone 28; and then evaporating the solvent from the coating to form an ion selective membrane 16 which coats the conductive surface at uninsulated zone 28 and coats and adheres to the insulating layer 22 generally surrounding zone 28.

As with electrode 10, in a further embodiment of electrode 20, a phospholipid or mixture of phospholipids is added in effective amount to the membrane formulation to extend the range of linear Nernstian response, and in yet other embodiments where appropriate, signal enhancing additives are added to the membrane formulation.

Conductive strip 24 of electrode 20 may be formed on the circuit board by any process known to the art. All of the materials which can be used for the electrically conductive member 14 of electrode 10 can be used for conductive member 24, but a copper strip coated with a thin layer of gold is preferred as this preserves the freshness of the conductive surface. Preferred materials for insulation layer 22 are the same as for insulation layer 12.

Another version of the process for electrode 20, further comprises forming insulation layer 22 on the surface of conductive strip 24 in a manner which permits a selected zone 28 on the surface of conductive strip 24 to remain free of insulation while being surrounded by insulation. This may preferably be accomplished by printing processes known in the art of circuit board manufacture, as well as well known coating, painting and spraying process. The insulation free zone is then coated as previously described.

All embodiments of the ion-selective electrode are preferably preactivated before use by exposure to an aqueous solution containing about $1 \times 10^{-3}$M to about $1 \times 10^{31}$ $^1$M of the ion to be detected for approximately 1 minute to approximately 12 hours, preferably for approximately 5 minutes to approximately 5 hours, and more preferably approximately 15 minutes to approximately 2 hours. The probe is then rinsed with deionized water and allowed to dry. Such preactivation of ion selective membranes is well known in the art. After preactivation the probe may be used directly or stored as previously described. The preactivation step may, however, be dispensed with when membrane 16 of electrode 10 is sufficiently thin to permit rapid equilibration with the ion to be sensed. Preactivation may generally avoided, although with some possible loss of sensitivity, with embodiments in which the thickness of the coating membrane 16 is preferably about 0,005 mm to about 0.4 mm, more preferably 0.01 mm to about 0.2 mm and most preferably 0.05 mm to about 0.1 mm. However, the membrane must be kept thick enough to retain sufficient mechanical strength for the intended use of the electrode 10.

The various embodiments of the present invention are used to determine the concentration of ions in a solution by measuring electromotive force (emf) against a standard reference electrode such as silver/silver chloride or calomel by methods well known in the art. The ion-selective electrode 10 is immersed at the end having the exposed conductor tip 18 coated by the membrane 16, in the same body of the test solution containing the ions to be detected with the reference electrode so that an electrical cell is formed. The ion-selective electrode 10 and the reference electrode are electrically connected via their non-immersed ends through an electromeric device for measuring emf such as a pH/mV meter or a high impedance electrometer. The resultant emf which is a function, as earlier described, of the concentration of the specific ion in the test solution to which the ion-selective electrode is sensitive, is read on the emf measuring device.

When using the electrode 10, it should be immersed in the test solution to a depth sufficient to cover the portion of the membrane 16 which coats the exposed conductor tip 18, preferably about 0.3 mm to about 5 mm and more preferably about 0.5 mm to 5 mm to obtain reliable results. When transferring the electrode 10 from one solution to another, it should be blotted dry and if necessary, preferably rinsed with a solution having ionic strength similar to the test solution in order to remove residues.

The embodiments of the invention are further illustrated by way of the following examples.

EXAMPLE 1

This example describes preparation and use of a version of the invention which is a pH sensor having the configuration shown in FIG. 1. The pH sensor was made by the following typical process. A PVC insulated 24 gauge copper wire (Woods ® No. 347, Woods Wire Products Inc.) was freshly cut with a pair of sharp wire cutters to attain a flat, clean surface. The wire was then coated with a membrane forming composition containing the following components dissolved in sufficient THF (Aldrich 99.5+% spectroscopic grade) to give a solution concentration of 20–35% by weight based on the total weight of the membrane forming composition components:

|  | Parts by Weight |
| --- | --- |
| PVC (Aldrich medium or high MW) | 250 |
| DOS (Sigma) | 718 |
| TPB (Fluka) | 2 |
| TDDA (Fluka) | 20 |
| PC (Sigma type II-S (10–20%) from soy bean) | 10 |

The membrane forming solution was then freed of air bubbles by mechanical shaking or gentle heating. The tip of the freshly cut wire was coated with the ion-selective membrane by immersing it vertically for a few seconds to a depth of 2 to 3 mm in the membrane forming solution. The coated wire was held in a vertical position with coated end down, in air for 30 minutes between coatings to allow for the evaporation of THF from the membrane. From 2–4 coats were applied in this manner until a coating of about 0.2 mm thickness was obtained on the tip of the wire. After the dip-coating process, the pH sensor was allowed to dry overnight in air. The pH sensor was pre-activated by placing it for 1 to 2 hours in a solution of HCl having a pH 3. It was then rinsed with deionized water and air dried.

The potentiometric response of the pH sensor was measured in mV at 20° C.±1° C. with a high impedance electrometer against a range of hydrogen ion concentrations, determined with a pH meter, in universal buffer containing 6.7 mM sodium citrate, 10 mM sodium phosphate, 11.4 mM boric acid and 28.9 mM sodium chloride. The reference electrode was silver/silver chloride immersed in agar saturated with silver chloride. Solution pH was adjusted with either HCl or NaOH.

Figure 2:
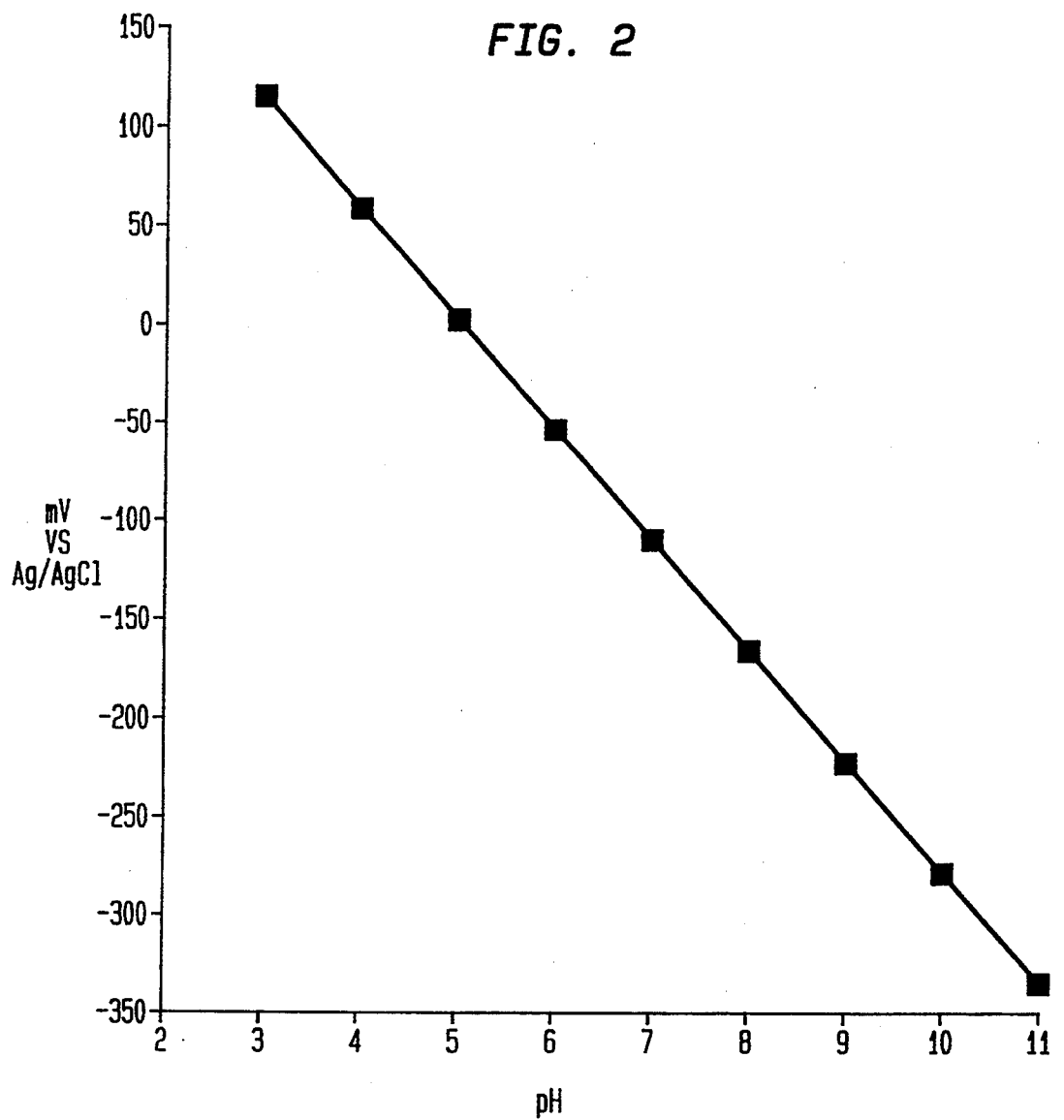
FIG. 2 shows a graph of the response of a pH sensing electrode version of the present invention in universal buffer.

A linear response was obtained from pH 3–11 with average slope 57 mV/pH. A plot of this is shown in FIG. 2.

EXAMPLE 2

The potentiometric response in mV of the pH sensor embodiment of Example 1, to changes of hydrogen ion concentration in artificial serum containing 0.51 mM calcium chloride, 0.47 mM dibasic ammonium phosphate, 0.16 mM magnesium chloride, 14 mM sodium chloride, 0.51 mM potassium chloride, 0.03 mM urea and 0.89 mM glucose, was measured at 20° C.±1° C., using a high impedance electrometer and a pH/mV meter. The reference electrode was silver/silver chloride immersed in agar saturated with silver chloride. Solution pH was adjusted with either HCl or NaOH.

A linear response was obtained from pH 4–8 with average slope 57 mV/pH. A plot of this is shown in FIG. 2A.

EXAMPLE 3

The potentiometric response in mV of the pH sensor embodiment of Example 1, to changes of hydrogen ion concentration in artificial urine containing 0.72 mM calcium chloride, 0.03 mM dibasic ammonium phosphate, 0.5 mM magnesium chloride, 13 mM sodium chloride, 4.3 mM potassium chloride and 2 mM urea, was measured at 20° C.±1° C., using a high impedance electrometer and a pH/mV meter. The reference electrode was silver/silver chloride immersed in agar saturated with silver chloride. Solution pH was adjusted with either HCl or NaOH.

A linear response was obtained from pH 4–8 with average slope 57 mV/pH. A plot of this is also shown in FIG. 2A.

EXAMPLE 3A

This example illustrates the advantage of PC in the membrane 16 of the pH sensor version of the invention. A sensor was prepared and preactivated as described in Example 1 except that PC was omitted from the membrane forming composition. This non-PC sensor was labelled DH9234. The performance of non PC sensor DH9234 was compared to a pH sensor made as described in Example 1 and labelled DH9238, by measuring the change of potential in mV with pH at 20° C.±1° C. against a range of hydrogen ion concentrations in universal buffer, as described in Example 1, using a high impedance electrometer and a pH/mV meter. The reference electrode was silver/silver chloride immersed in agar saturated with silver chloride.

A linear response was obtained for the sensor DH9238 containing PC in the membrane 16, from pH 3–11 with average slope 57 mV/pH. The sensor DH9234 not having PC in the membrane 16 gave a linear response from pH 11 to pH 5 with slope about 55 mV/pH, but below pH 5, however, the slope was super-Nernstian with a value of about 67 mV/pH and is unstable relative to sensor DH9238. A comparative plot of this from pH 3–11 is shown in FIG. 2B. FIG. 2C shows an enlarged view from pH 3–7.

EXAMPLE 4

This example describes preparation and use of a version of the invention which is a potassium selective ion sensor having the configuration shown in FIG. 1. The sensor was prepared using the general procedure and wire described in Example 1 and the membrane forming composition described below. The sensor was not preactivated. The membrane forming composition contained the following components dissolved in sufficient THF (Aldrich 99.5+% spectroscopic grade) to give a solution concentration of 20–35% based on the total weight of the components:

|  | Parts by Weight |
| --- | --- |
| PVC (Aldrich medium or high MW) | 250 |
| CB (Aldrich) | 10 |
| TPB (Fluka) | 2 |
| DBP (Aldrich) | 668 |

|  | Parts by Weight |
| --- | --- |
| Valinomycin | 60 |
| PC (Sigma type II-S (20%) from soy bean) | 10 |

Figure 3:
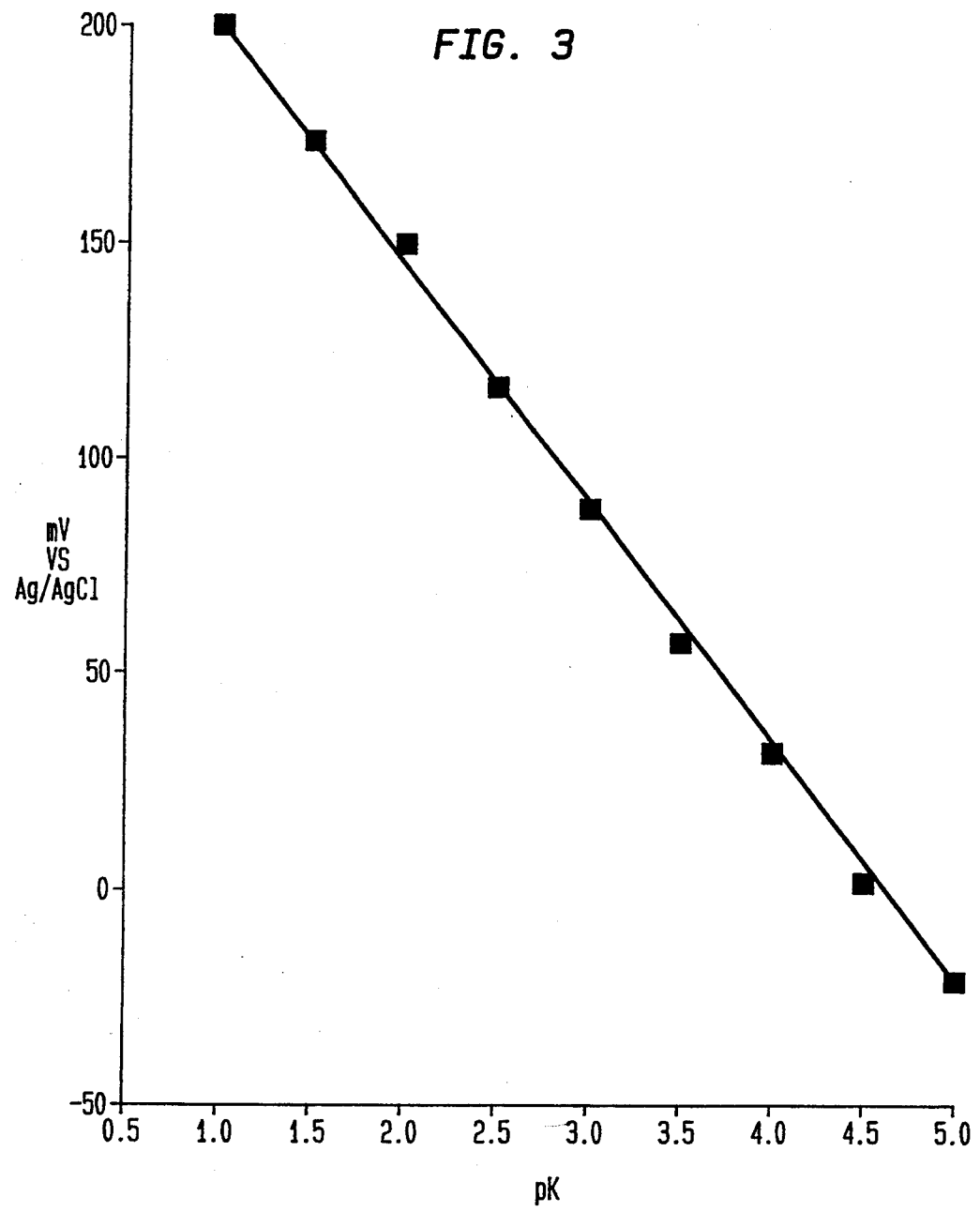
FIG. 3 shows a graph of the response of a potassium ion sensing electrode version of the present invention.

The potentiometric response in mV of the potassium selective ion sensor with change in potassium ion concentration in aqueous solution was measured at 20° C.±1° C. using either a high impedance electrometer or a pH/mV meter. The reference electrode was silver/silver chloride immersed in agar saturated with silver chloride. A linear response was observed from $10^{-5}$M to $10^{-1}$M K$^+$ with an average slope of 58 mV/decade r concentration. A plot of this is shown in FIG. 3. Another potassium selective sensor prepared as described here, except that the sensor membrane 16 did not contain PC, gave the same response.

EXAMPLE 5

This example describes preparation and use of a version of the invention which is a sodium selective ion sensor having the configuration shown in FIG. 1. The sensor was prepared using the general procedure and wire described in Example 1 and the membrane forming composition described below. The sensor was preactivated in $10^{-2}$M NaCl overnight. The membrane forming composition contained the following components dissolved in sufficient THF (Aldrich 99.5+% spectroscopic grade) to give a solution concentration of 20–35% based on the total weight of the components:

|  | Parts by Weight |
| --- | --- |
| PVC (Aldrich medium or high MW) | 268 |
| NPOE (Sigma) | 622 |
| CMMDM (Sigma) | 100 |
| PC (Sigma type II-S (20%) from soy bean) | 10 |

Figure 4:
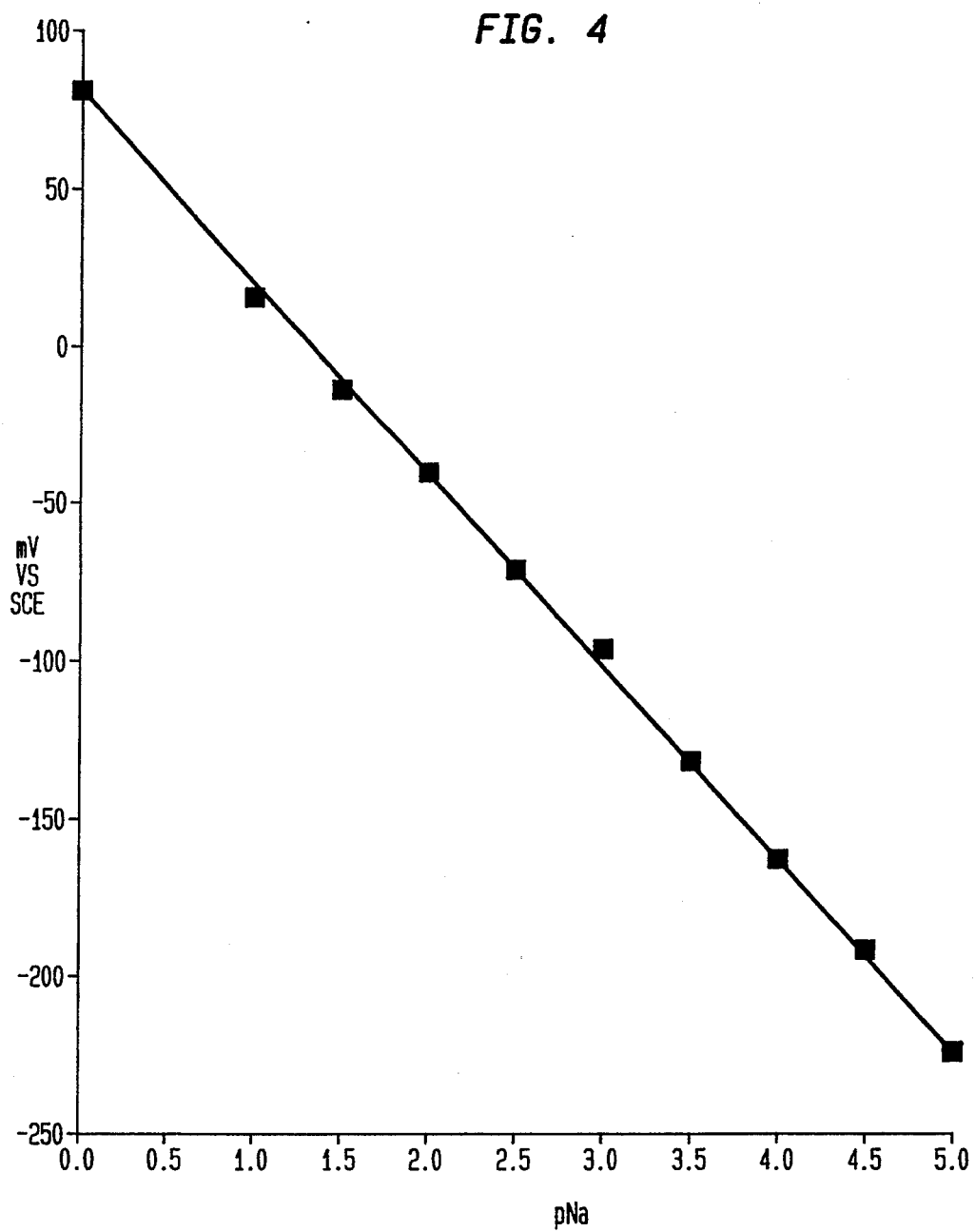
FIG. 4 shows a graph of the response of a sodium ion sensing electrode version of the present invention.

The potentiometric response in mV of the sodium selective ion sensor with change in sodium ion concentration in aqueous solution was measured at 20° C.±1° C. using either a high impedance electrometer or a pH/mV meter. The reference electrode was a standard calomel electrode (SCE). A linear response to sodium ion concentration was observed from $10^{-5}$M to $10^{-1}$M Na$^+$ with an average slope of 59 mV/decade Na$^+$ concentration. A plot of this is shown in FIG. 4.

Example 5A

This example illustrates the advantage of PC in the membrane 16 of the selective sodium ion sensor version of the invention. A sensor was prepared as described in Example 5 except that PC was omitted from the membrane forming composition. The performance of the sensor not having PC in the membrane 16 was compared to the sodium ion sensor prepared as described in Example 5, having PC in the membrane 16, by measuring the change of potential in mV with change of sodium ion concentration from $10^{-5}$M to 1M in aqueous medium at 20° C.±1° C. as described in Example 5. The selective sodium ion sensor having PC in membrane 16 gave a linear response throughout this entire range with slope about 57 mV/decade of concentration, while the sensor not having PC in the sensor membrane was linear only from $10^{-3}$–1M. A plot of this is shown in FIG. 4A.

The previously described versions of the present invention have many advantages, including ease and simplicity of preparation and use. They may be readily made in a few steps from inexpensive materials such as insulated copper wire by simply cutting it and dip coating the newly created metallic surface with a readily formulated ion selective membrane forming solution. The simplicity of this process which is done in relatively few steps makes for a high degree of consistency among individual sensors and from batch to batch. Another advantage is the higher degree of mechanical stability achieved as a consequence of good adhesion of the ion-selective membrane to the surface of the underlying conductor and to the layer of insulation covering the conductor. This improved mechanical stability makes the ion sensors of the present invention less fragile and easier to use. A further advantage of improved mechanical stability is extended shelf life as well as increased operational lifetime.

The extended shelf life and operational lifetime are especially advantageous when compared to conventional electrodes using lipid membranes in the form of a bilayer or a combination of monolayers.

An additional advantage is that they are easy to use as they are easily calibrated with a single point because they have a widened linear Nernstian response range. Yet another additional advantage is that the small surface area of the active sensor site allows small quantities of test solution to be used. Yet another advantage is that their high sensitivity makes it possible to reliably assay even low concentrations of ions in very small volumes of test media such as biological fluids.

Still another advantageous feature is that the active sensor surface of versions of the present invention may be confined to about the area of the cross-section of a fine wire using the process of the invention thus answering the need for sensors which can be readily miniaturized.

A further advantage of versions of the present invention is that since they can be made by a simple, inexpensive process from low cost materials or very small quantities of more expensive materials, from an economic point of view, they may be disposed of after even a single use if this is desired.

Although the present invention has been described in considerable detail with reference to certain preferred versions thereof, other versions are possible. For example, other versions of the ion-selective sensor are possible as is its use in conjunction with instrumentation such as titrametric devices. Therefore, the spirit and scope of the appended claims should not be limited to the description of the preferred versions contained herein.

What is claimed is:

1. An ion-selective electrode comprising:
   an electrically conductive member sheathed with a layer of polymeric electrical insulation, said polymeric electrical insulation in direct contact with said electrically conductive member, the conductive member having an uninsulated zone surrounded by the polymeric insulation, and
   an ion-selective membrane which completely coats and is in direct contact with the uninsulated zone of the conductive member and overlays and adheres to the surrounding insulation,
   said ion selective membrane comprising,
   a polymer matrix, the polymeric matrix having dispersed or dissolved therein,
   a plasticizer, and
   an ionophore sensitive to an ion of interest, and a phospholipid.

2. The ion-selective electrode of claim 1 in which the electrically conductive member is selected from the group consisting of copper, silver, conductive carbon, gold, aluminum, platinum, nickel, stainless steel, iron and, mixtures and, laminates thereof.

3. The ion-selective electrode of claim 2 in which the electrically conductive member is a wire with the uninsulated zone corresponding to a tip of the wire.

4. The ion-selective electrode of claim 3 in which the wire is comprised of copper.

5. The ion-selective electrode of claim 2 in which the electrically conductive member is a strip formed on an electrical circuit board base with the uninsulated zone on the surface of said strip.

6. The ion-selective electrode of claim 5 in which the strip is a laminate comprising a layer of copper in contact with the circuit board base, said layer of copper having a gold coating, with the uninsulated zone on the gold coating.

7. The ion-selective electrode of claim 1 in which the layer of electrical insulation is comprised of a polymeric material selected from the group consisting of polyvinylchloride, copolymers of polyvinylchloride, polymers compatible with polyvinylchloride, polyethylene, polypropylene, nylon, and silicone rubber.

8. The ion-selective electrode of claim 7 in which the layer of electrical insulation is comprised of a polymeric material selected from the group consisting of polyvinylchloride, copolymers of polyvinylchloride, polymers compatible with polyvinylchloride and mixtures thereof.

9. The ion-selective electrode of claim 8 in which the polymer matrix, comprising the ion selective membrane, is formed from a polymer selected from the group consisting of polyvinylchloride, copolymers of polyvinylchloride, polymers compatible with polyvinylchloride and mixtures thereof.

10. The ion-selective electrode of claim 9 in which the plasticizer is chosen from the group consisting of 2-nitrophenyl alkyl ether, dioctylphthalate, dibutylphthalate, dipentylphthalate, bis(2-ethylhexyl) sebacate and other di-n-alkyl sebacates, oxalic acid derivatives and mixtures thereof.

11. The ion-selective electrode of claim 1 in which the ionophore is a substance sensitive to an ion chosen from the group consisting of hydrogen ions, potassium ions or sodium ions.

12. The ion-selective electrode of claim 1 in which the phospholipid is chosen from the group consisting of:

wherein $R^1$, and $R^2$ are acyl groups derived from saturated or unsaturated fatty acids having from 6 to 24 carbon atoms, and $R^3$ is $-CH_2CH^2N(R^4)_2$ and the protonated form thereof, $-CH_2CH_2N^+(R^4)_3$ or $-CH_2CHN(R_4)_2CO_2H$ and charged forms thereof, wherein $R^4$ is chosen from the group consisting of H, alkyl groups having from 1–14 carbon atoms or benzyl in any combination, and $R^3$ is further inositolyl, $-CH_2CHOHCH_2OR_5$ wherein $R_5$ is H or $CH_2OR^1CHOR^2CH_2OP(=O)(-O^-)-$ and protonated forms thereof, sphingomyelin; and mixtures thereof.

13. The ion-selective electrode of claim 12 in which the phospholipid is phosphatidylcholine.

14. The ion-selective electrode of claim 13 in which the phosphatidylcholine comprises at least about 10% of a mixture derived from soy beans, said mixture containing other lipids.

15. The ion-selective electrode of claim 1, 12, 13 or 14 in which the ion-selective membrane further includes signal enhancing compounds chosen from the group consisting of potassium tetrakis (4-chlorophenyl) borate, sodium tetraphenylborate, iodine, β-carotene, chlorobenzene, nitrobenzene and mixtures thereof.

16. A process for making an ion-selective electrode having a structurally strong ion-selective membrane comprising the steps of:
   a) forming an electrically conductive member electrically insulated with a layer of polymeric electrical insulation, said polymeric electrical insulation in direct contact with said electrically conductive member, the conductive member having an uninsulated zone surrounded by the insulation;
   b) preparing a liquid solution comprising an ion-selective polymeric membrane formulation by dispersing a polymer, a plasticizer, an ionophore and a phospholipid in a solvent;
   c) coating the uninsulated zone of said electrically conductive member, so that the liquid solution coats, and is in direct contact with said uninsulated zone of the conductive member, and coats the polymeric electrical insulation generally adjacent to and surrounding the uninsulated zone of the conductive member;
   d) evaporating the solvent to form an ion selective membrane which coats, and is in direct contact with the uninsulated zone of the conductive member, and overlays and adheres to the polymeric electrical insulation surrounding and generally adjacent to the uninsulated zone, thereby forming an ion-selective electrode with a structurally strong membrane.

17. The process of claim 16 in which the electrically conductive member of step a) is selected from the group consisting of copper, silver, conductive carbon, gold, aluminum, platinum, nickel, stainless steel, iron and, mixtures and, laminates thereof.

18. The process of claim 17 in which the insulated electrically conductive member is an insulated wire and the insulation free zone surrounded by insulation is a tip of the insulated wire formed by cutting the wire.

19. The process of claim 17 in which the insulated electrically conductive member is a metallic strip mounted on a circuit board base and the insulation free zone surrounded by insulation is formed by a printing process.

20. The process of claim 19 in which the strip is a laminate comprising a layer of copper in contact with the circuit board base, said layer of copper having a gold coating, with the uninsulated zone on the gold coating.

21. The process of claim 18 in which the wire is copper.

22. The process of claim 16 in which the layer of polymeric electrical insulation is comprised of a polymeric material selected from the group consisting of polyvinylchloride, copolymers of polyvinylchloride, polymers compatible with polyvinylchloride, polyethylene, polypropylene, nylon, and silicone rubber.

23. The process of claim 22 in which the layer of polymeric electrical insulation is comprised of a polymeric material selected from the group consisting of polyvinylchloride, copolymers of polyvinylchloride, polymers compatible with polyvinylchloride and mixtures thereof.

24. The process of claim 23 in which the polymer matrix, comprising the ion selective membrane, is formed from a polymer selected from the group consisting of polyvinylchloride, copolymers of polyvinylchloride, polymers compatible with polyvinylchloride and mixtures thereof.

25. The process of claim 16 in which the phospholipid is chosen from the group consisting of:

wherein $R^1$, and $R^2$ are acyl groups derived from saturated or unsaturated fatty acids having from 6 to 24 carbon atoms, and $R^3$ is $-CH_2CH_2N(R^4)_2$ and the protonated form thereof, $-CH_2CH_2N^+(R^4)_3$ or $-CH_2CHN(R^4)_2CO_2H$ and charged forms thereof, wherein $R^4$ is chosen from the group consisting of H, alkyl groups having from 1–14 carbon atoms or benzyl in any combination, and $R^3$ is further inositolyl, $-CH_2CHOHCH_2OR_5$ herein $R_5$ is H or $CH_2OR^1CHOR^2CH_2OP(=O)(-O^-)-$ and protonated forms thereof, sphingomyelin; and mixtures thereof.

26. The process of claim 25 in which the phospholipid is phosphatidylcholine.

27. The process of claim 26 in which the phosphatidylcholine comprises at least about 10% of a mixture derived from soy beans, said mixture containing other lipids.

28. The process of claim 16, 25, 26 or 27 in which step b) further comprises mixing into the polymeric membrane formulation a signal enhancing compound chosen from the group consisting of potassium tetrakis (4-chlorophenyl) borate, sodium tetraphenylborate, iodine, β-carotene, chlorobenzene, nitrobenzene and mixtures thereof.

29. An ion-selective electrode with increased sensitivity to ions in aqueous solution fabricated in steps comprising:
   a) forming an electrically conductive member electrically insulated with a layer of polymeric electrical insulation, said polymeric electrical insulation in direct contact with said electrically conductive member, the conductive member having an uninsulated zone surrounded by the insulation;
   b) preparing a liquid solution of an ion-selective membrane formulation by dispersing a polymer, a plasticizer, an ionophore and a phospholipid in a solvent;
   c) coating the insulation free zone and the insulation generally adjacent to said zone with the liquid solution so that the liquid solution forms a coating which envelops said zone and overlays the generally adjacent surrounding insulation;
   d) evaporating the solvent to form an ion-selective membrane which coats, and is in direct contact with the uninsulated zone of the conductive member, and overlays and adheres to the polymeric electrical insulation surrounding and generally adjacent to the uninsulated zone.

30. The electrode of claim 29 in which the layer of polymeric electrical insulation is comprised of a polymeric material selected from the group consisting of polyvinylchloride, copolymers of polyvinylchloride, polymers compatible with polyvinylchloride and mixtures thereof.

31. The electrode of claim 30 in which the polymer matrix, comprising the ion selective membrane, is formed from a polymer selected from the group consisting of polyvinylchloride, copolymers of polyvinylchloride, polymers compatible with polyvinylchloride and mixtures thereof.

32. The electrode of claim 31 in which the phospholipid is phosphatidylcholine.

33. The electrode of claim 32 in which the phosphatidylcholine comprises at least about 10% of a mixture derived from soy beans, said mixture containing other lipids.

34. The electrode of claim 29 in which the phospholipid is chosen from the group consisting of:

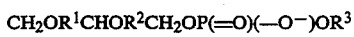

wherein $R^1$, and $R^2$ are acyl groups derived from saturated or unsaturated fatty acids having from 6 to 24 carbon atoms, and $R^3$ is —$CH^2CH_2N(R^4)_2$ and the protonated form thereof, —$CH_2CH^2N^+(R^4)_3$ or —$CH_2CHN(R^4)_2CO_2H$ and charged forms thereof, wherein $R^4$ is chosen from the group consisting of H, alkyl groups having from 1–14 carbon atoms or benzyl in any combination, and $R^3$ is further inositolyl, —$CH_2$-$CHOHCH_2OR_5$ wherein $R_5$ is H or $CH_2OR^1CHOR^2C$-$H_2OP(=O)(-O^-)$— and protonated forms thereof, sphingomyelin; and mixtures thereof.

35. The electrode of claim 29, 34, 32 or 33 in which the ion-selective membrane further includes signal enhancing compounds chosen from the group consisting of potassium tetrakis (4-chlorophenyl) borate, sodium tetraphenylborate, iodine, β-carotene, chlorobenzene, nitrobenzene and mixtures thereof.

36. A polymeric ion-selective membrane to interface with a test solution containing ions, the membrane in direct contact with a conductive substrate or in electrical contact with an internal reference electrode element, said membrane comprising:
   a polymeric matrix, the polymeric matrix having dispersed or dissolved therein;
   a plasticizer,
   an ionophore, and
   a phospholipid chosen from the group consisting of:

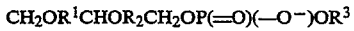

wherein $R^1$, and $R^2$ are acyl groups derived from saturated or unsaturated fatty acids having from 6 to 24 carbon atoms, and $R^3$ is —$CH_2CH_2N(R^4)_2$ and the protonated form thereof, —$CH_2CH_2N^+(R^4)_3$ or —$CH_2CHN(R^4)_2CO_2H$ and charged forms thereof,
wherein $R^4$ is chosen from the group consisting of H, alkyl groups having from 1–14 carbon atoms or benzyl in any combination, and $R^3$ is further inositolyl, —$CH_2$-$CHOHCH_2OR_5$ wherein $R_5$ is H or $CH_2OR^1CHOR^2C$-$H_2OP(=O)(-O^-)$— and protonated forms thereof, sphingomyelin; and mixtures thereof.

37. The membrane of claim 36 in which the phospholipid is phosphatidylcholine.

38. The membrane of claim 37 in which the phosphatidylcholine comprises at least about 10% of a mixture derived from soy beans, said mixture containing other lipids.

39. An ion-selective coated wire electrode comprising:
   a copper wire sheathed with a layer of polymeric electrical insulation comprised of polyvinylchloride, said polymeric electrical insulation comprised of polyvinylchloride in direct contact with said copper wire, said copper wire having an uninsulated tip;
   a polymeric ion-selective membrane which completely coats and is in direct contact with the uninsulated tip of the copper wire and overlays and adheres to the surrounding insulation;
   said polymeric ion-selective membrane comprising;
      a polymer matrix formed from a polymer comprising polyvinylchloride, the polymer matrix having dispersed therein,
      a plasticizer chosen from the group consisting of 2-nitrophenyl octyl ether, bis (2-ethylhexyl) sebacate dibutyl phthalate,
      an ionophore chosen from the group consisting of tridodecylamine, bis([12-crown-4]-2-methyl)2-methyl-2-dodecylmalonate, and
      further containing phosphatidylcholine dispersed therein, the phosphatidylcholine comprising about 10% to about 20% of a mixture derived from soy beans, said mixture containing other lipids.

40. The coated wire electrode of claim 39, in which the amount of phosphatidylcholine is at least about 0.01% based on the total weight of the components comprising the membrane.

41. The coated wire electrode of claim 40 in which the ionophore is tridodecylamine and in which the membrane further comprises potassium tetrakis (4-chlorophenyl) borate.

* * * * *